United States Patent [19]

Fischell et al.

[11] Patent Number: 5,409,454
[45] Date of Patent: Apr. 25, 1995

[54] APPARATUS FOR ATHERECTOMY

[75] Inventors: Robert E. Fischell, Dayton, Md.;
James J. Thompson, Reading, Pa.;
David R. Fischell, Fair Haven, N.J.;
Richard L. Harding, Reinholds, Pa.;
Tim A. Fischell, Los Altos, Calif.

[73] Assignee: Arrow International Investment Corp., Wilmington, Del.

[21] Appl. No.: 236,249

[22] Filed: May 2, 1994

Related U.S. Application Data

[63] Continuation of Ser. No. 939,394, Aug. 31, 1992, abandoned, which is a continuation of Ser. No. 656,600, Feb. 19, 1991, abandoned.

[51] Int. Cl.$^6$ .............................................. A61B 17/22
[52] U.S. Cl. ...................................... 604/22; 606/159
[58] Field of Search ...................... 606/159, 170, 171; 128/751, 753, 754; 604/22

[56] References Cited

U.S. PATENT DOCUMENTS

| | | | |
|---|---|---|---|
| 4,669,469 | 6/1987 | Gifford et al. | 606/159 |
| 4,765,332 | 8/1988 | Fischell et al. | 606/159 |
| 4,781,186 | 11/1988 | Simpson et al. | 606/171 |
| 4,846,192 | 7/1989 | MacDonald | 606/159 X |
| 4,867,156 | 9/1989 | Stack et al. | 606/159 |
| 4,950,238 | 8/1990 | Sullivan | 606/159 X |
| 4,994,067 | 2/1991 | Summers | 604/22 |
| 5,087,265 | 2/1992 | Summers | 606/159 |
| 5,092,873 | 3/1992 | Simpson et al. | 606/159 |

Primary Examiner—Michael H. Thaler
Attorney, Agent, or Firm—Morton J. Rosenberg; David I. Klein

[57] ABSTRACT

A catheter is disclosed which is capable of cutting obstructive tissue from a vessel of a living body while shielding a portion of the wall of the vessel from being exposed to the cutting blade at the catheter's distal end. An essentially continuous outer surface at the catheter's distal end allows it to be readily advanced through an introducer sheath and through a tight stenosis in an artery. The shield at the catheter's distal end could subtend an arc from as little as 45 degrees to as large as 270 degrees depending on the extent of the vessel wall that is to be protected from being cut. A vacuum source at the catheter's proximal end can cause a suction to exist at a cutout at the catheter's distal end in order to pull obstructive tissue into the cutout as the cutting cylinder is pulled back in a retrograde direction, this suction being capable of enhancing the removal of the obstructive tissue.

13 Claims, 9 Drawing Sheets

APPARATUS FOR ATHERECTOMY

This is a continuation of application Ser. No. 07/939,394, filed on 31 Aug. 1992, now abandoned, which is a continuation of application Ser. No. 07/656,600, filed on Feb. 19, 1991, now abandoned.

BACKGROUND OF THE INVENTION

1. Field of the Invention

This invention constitutes an improved means and method for excising plaque from stenoses in human arteries including those which have an eccentrically located lumen by employing the method termed Vacuum Pullback Atherectomy (VPA) and using the Shielded Pullback Atherectomy Catheter (SPAC).

2. Description of the Prior Art

U.S. Pat. No. 4,765,332 entitled "Pullback Atherectomy Catheter System" which issued on Aug. 23, 1988 to R. E. Fischell and T. A. Fischell and is incorporated herein by reference teaches an atherectomy catheter that cuts in the retrograde direction. The design taught by the Fischells is however not well suited to excise plaque from highly eccentric stenoses. Furthermore, the U.S. Pat. No. 4,765,332 patent does not teach any way to excise plaque so that the final luminal diameter of the stenosis undergoing atherectomy is larger than the diameter of the catheter's distal end.

U.S. patent application Ser. No. 577,633, now U.S. Pat. No. 5,127,902 by Robert E. Fischell filed on Sep. 5, 1990 and entitled "Apparatus and Method for Precisely Controlling the Excision of Obstructive Tissue in a Human Blood Vessel" which is incorporated herein by reference, is an improvement in the atherectomy art in that it describes a means and method for excising plaque so that the final luminal diameter of the stenosis is larger than the diameter of the catheter's distal end. However, this cited patent application teaches an atherectomy means and method which requires a pressure cuff to be applied externally to the limb of the body being treated. Thus, deep internal arteries such as coronary arteries which cannot readily have a pressure cuff placed around the surrounding tissue are not able to be treated using the invention taught in that patent application.

In 1989, B. F. Waller, M.D. authored an article entitled "The Eccentric Coronary Atherosclerotic Plaque: Morphologic Observations and Clinical Relevance" which states that 73% of 500 coronary artery stenoses that he studied had an eccentric lumen. Dr. Waller defines an eccentric stenosis as one in which at least some arc length of the arterial wall is not significantly thickened with plaque. Of the 365 coronary arteries with eccentric stenoses that Dr. Waller studied, he reported that the arc length of disease-free wall measured from 2.3% to 32% of the vessel circumference with a mean of 16.6%. This corresponds to angular arcs of 8° minimum, 115° maximum and 60° mean arc length.

From Dr. Waller's careful studies it becomes apparent that for most cases of atherectomy of the coronary arteries it is highly desirable to have an atherectomy catheter that would shield this arc of disease-free wall while excising the plaque that is attached to the remaining arc of the diseased arterial wall.

Some of the earliest prior art that addresses the problem of atherectomy of both concentric and eccentric stenoses is the European Patent Application 0,163,502 entitled "Atherectomy Device and Method" by J. B. Simpson having a priority date of May 5, 1984. This Simpson patent application teaches an anterograde cutter on a flexible cable that moves within a generally cylindrical housing having a rounded metallic distal end. The housing has a longitudinally extending cutout which typically makes up an arc of approximately 90°; i.e. the rigid metal portion of the housing is shown to have an arc of approximately 270°. A balloon is secured to the housing opposite the cutout. When the balloon is inflated, the cutout is pressed into the plaque on the opposite side of the arterial wall. This makes it possible for the rotating, anterograde sliding cutter to shave off the plaque and push it into a plaque collection chamber located within the distal, rounded end of the housing. Although the design taught by Simpson in this European Patent Application has been successfully used to excise plaque from human arteries, it has several significant shortcomings especially when used in tortuous coronary arteries. Brief descriptions of the deficiencies of this Simpson design are as follows:

(1) The rigid, rounded distal end of the housing is not an efficient shape for Dottering (pushing) through a tight stenosis and does not track well over a guide wire.

(2) For the over-the-wire design illustrated in FIGS. 1, 2, and 3 of the Simpson Application, the guide wire passes through the plaque collection chamber. Thus, plaque is packed into the plaque collection chamber tightly around the guide wire. Therefore, the guide wire becomes locked into the plaque, and therefore, the guide wire must be removed when the catheter is removed. This is a significant operational shortcoming of this structural design because placing the catheter back into the artery also requires replacing and repositioning the guide wire.

(3) The embodiment showing a fixed guide wire at the housing's distal end (FIG. 7), will of course, also require the guide wire to be removed from the artery when the catheter is removed. This is a disadvantageous design as compared to an over-the-wire system (not however as implemented in the Simpson design) in which the guide wire can remain in place while the catheter is pushed in and/or out one or more times into the artery that is undergoing atherectomy.

(4) Since some coronary arteries exhibit considerable tortuosity, it is highly desirable to minimize the rigid length (and therefore the volume) of the housing while maximizing the length of the plaque collection chamber. The Simpson design is disadvantageous in that it teaches a comparatively long rigid housing with only a very short length devoted to storage of the cut plaque.

(5) Because the cutter pushes in the anterograde direction (as opposed to the retrograde direction) the force that can be exerted by the flexible cable is limited.

(6) The comparatively sharp metal edges of the housing cutout are disadvantageous because they make it more difficult to Dotter through a long, tight stenosis. This is because these sharp metal edges can be caught in a tight stenosis and prevent passage of the distal end of the catheter. Furthermore, this design prevents easy passage of the housing cutout through the proximal valve of an introducer sheath which is another significant disadvantage.

(7) Because the cutter is on a flexible cable, the cutout must be considerably less than 180° in arc or else the cutter could pop out of the housing as it slides forward in the anterograde direction for example when the cutter would engage some calcified plaque. This limits the arc of plaque that can be cut on any single forward cutting pass of the cutter. Thus, with a 90° arc of the cutout, the housing must typically be rotated at least four times around its longitudinal axis in order to collect plaque around all 360° of arc around the arterial wall. This makes for a comparatively time consuming and arduous atherectomy.

(8) The plaque must first be collected in the cutter and then transferred to the plaque collection section of the housing. This design is comparatively complex when compared to simply collecting the plaque within the cutter itself and leaving it there.

(9) The inflatable balloon which is taught in the Simpson design adds to the catheter's complexity, increases the effective diameter at the catheter's distal end and decreases system reliability because it may fail to inflate or deflate or it may burst. Furthermore, balloon inflation can cause intimal dissection of the artery which is clearly an undesirable outcome of atherectomy.

(10) The sharpened edge of the cutter can engage the metal, distal interior portion of the housing while spinning and therefore can become dull after a single usage. This is disadvantageous when, as is typically necessary, repeated cuts are required.

Two additional prior art patents, namely U.S. Pat. No. 4,669,469 by H. S. Gifford, III and J. B. Simpson and U.S. Pat. No. 4,781,186 by J. B. Simpson et al, teach art comparable to that taught in the above referenced European Patent Application by J. B. Simpson. Each of these two U.S. patents have virtually all the shortcomings described in items (1) through (10) inclusive above.

SUMMARY OF THE INVENTION

One embodiment of the present invention is a retrograde cutting atherectomy catheter that overcomes the numerous shortcomings of the prior art devices that are listed herein. This specially designed Shielded Pullback Atherectomy Catheter (SPAC) system consists of four basic subsystems which are as follows:
(1) A flexible guide wire,
(2) A cut/collect catheter having a central passageway through which the guide wire can be passed,
(3) A shielding catheter which moves concentrically and slideably along the cut/collect catheter, and
(4) A rotating means attachable at the cut/collect catheter's proximal end which can rotate the cut/collect catheter as it is being pulled back in the retrograde direction.

The first three items listed above are termed herein as the "SPAC".

Additionally, the technique of Vacuum Pullback Atherectomy (VPA) can be accomplished with the addition of one or both of the following systems:
1. A vacuum source attachable at the shielding catheter's proximal end to one lumen which is in fluid communication with an opening at the shielding catheter's distal end, and
2. A source of an inflation fluid which is attached at the shielding catheter's proximal end to a second lumen of the shielding catheter which is in fluid communication with an occlusive balloon located at the shielding catheter's distal end.

Another embodiment of this invention involves the technique termed Compressional Pullback Atherectomy (CPA), as described in the aforementioned U.S. patent application Ser. No. 577,633. CPA can be accomplished in peripheral arteries such as those in the legs, arms or neck by the combination of the basic four SPAC subsystems, plus a blood pressure cuff or equivalent that surrounds the part of the body where the stenosis is located. The pressure cuff is inflated to a comparatively high pressure to squeeze the stenotic plaque into the open distal end of cut/collect catheter.

Thus one object of the present invention is to perform atherectomy using a vacuum within the region of an arterial stenosis so as to bring the stenotic plaque into a position where it can be cut so that after the vacuum is removed the luminal diameter at the site of the stenosis is greater than the outside diameter of the catheter doing the cutting.

Another object of the present invention is to perform atherectomy on an eccentric stenosis by cutting plaque from one part of an arterial wall while shielding a normal portion of the arterial wall from being cut.

Still another object of the present invention is to accomplish atherectomy with a catheter that has a flexible and tapered distal end and a continuous outer surface (i.e. free of an open window) when it is inserted into or removed from the artery so that it can be easily advanced through an introducer sheath and through a tight stenosis or total occlusion.

Still another object of the present invention is to achieve the objects listed above with an over-the-wire atherectomy catheter system which allows the guide wire to remain in the artery after the plaque is packed into the plaque collection chamber.

Still another object of the present invention is to use the SPAC design of catheter in combination with externally applied compression.

Still other objects of the present invention will become clear as the drawings of the various embodiments of this invention are described herein.

DETAILED DESCRIPTION OF THE DRAWINGS

Figure 1:
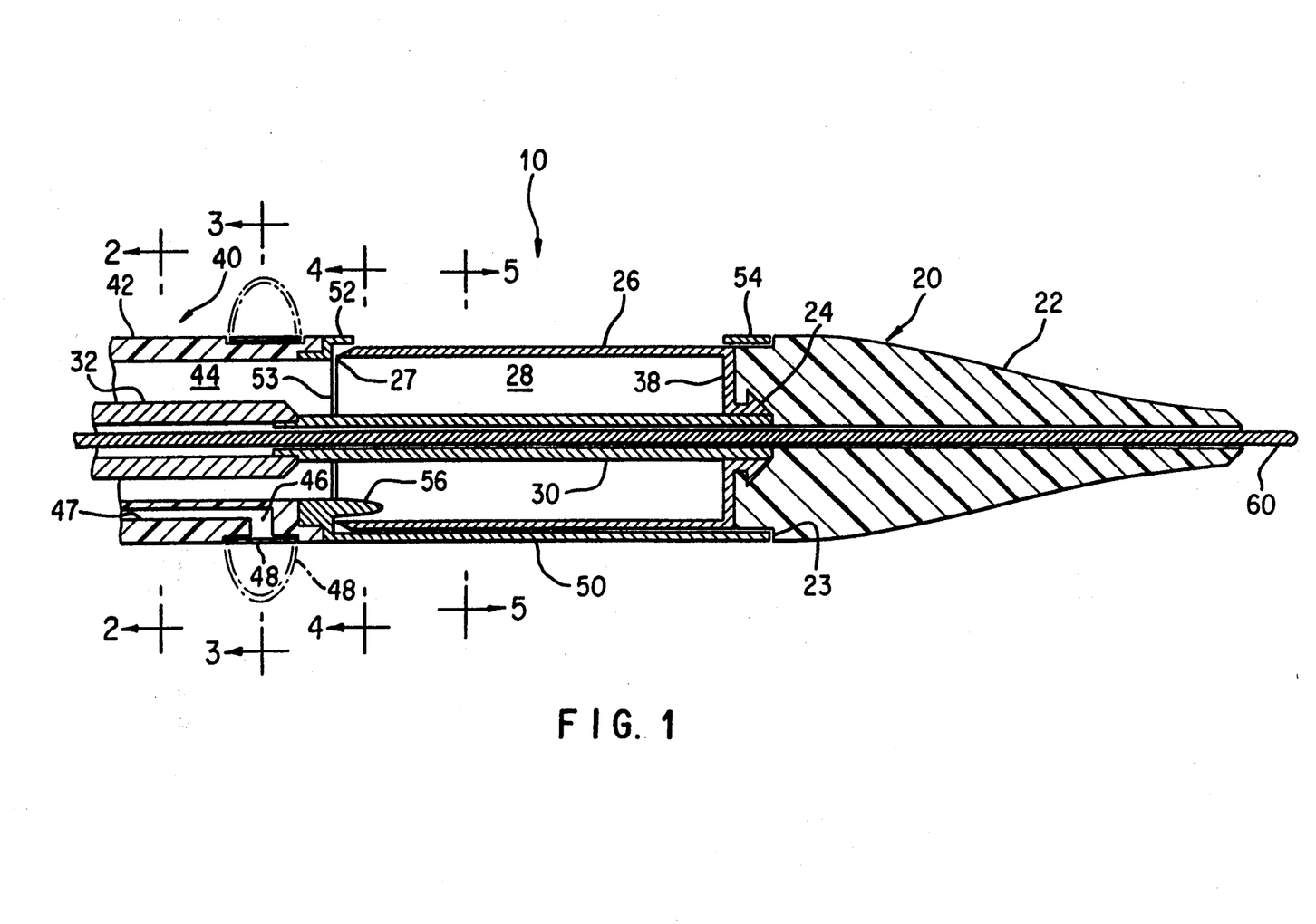
FIG. 1 is a longitudinal cross section of the distal end of the SPAC catheter shown in its closed position.
Figure 11:
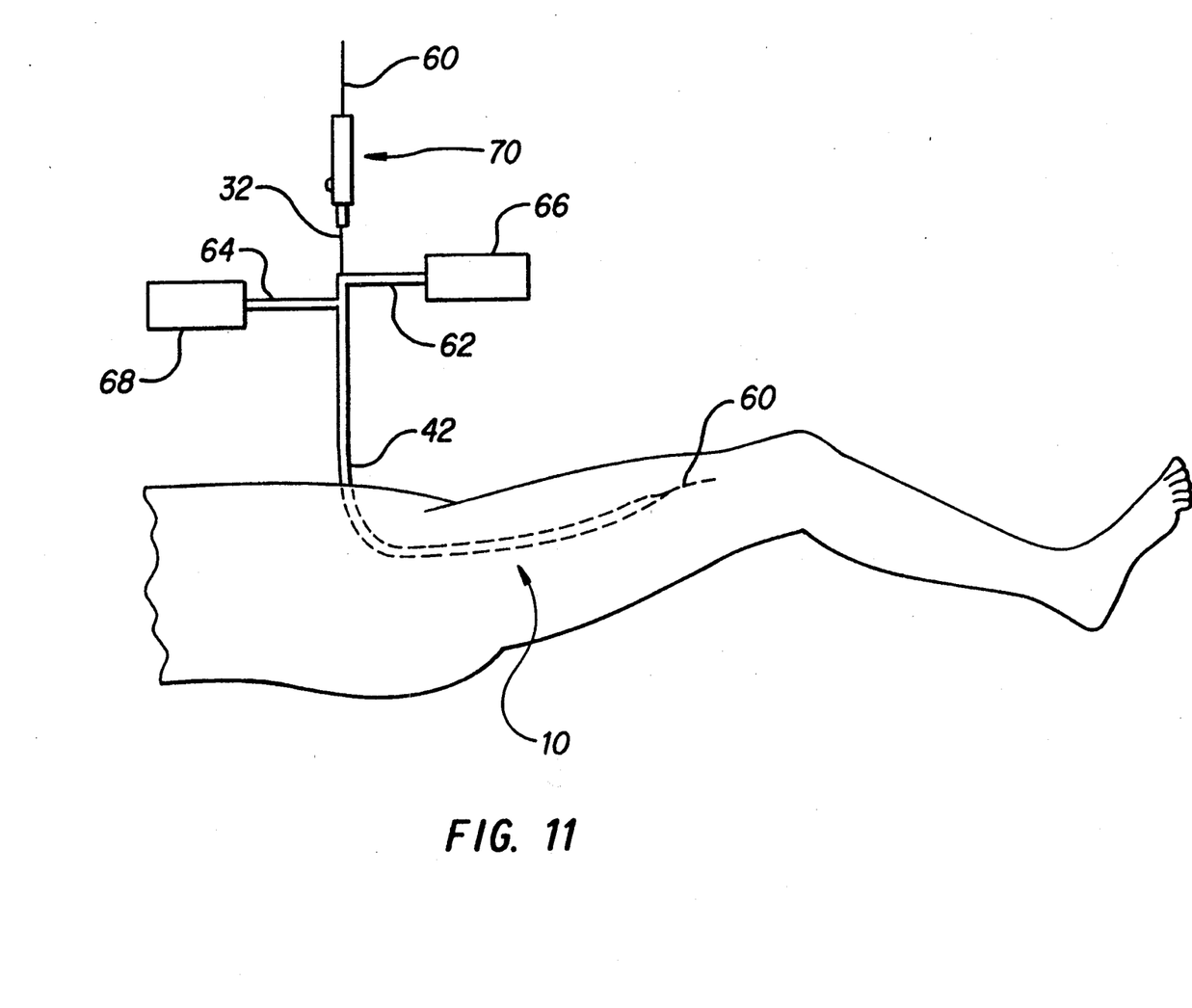
FIG. 11 shows the SPAC system being used for atherectomy in a human leg.

FIG. 1 is a longitudinal cross-sectional view showing the distal end of the SPAC in the closed position. The SPAC 10 consists of 3 principal parts: the guide wire 60, the cut/collect catheter 20, and the shielding catheter 40. From FIG. 1 we see that the cut/collect catheter 20 has a cutting cylinder 26 which has a sharpened edge 27 at its proximal end and at its distal end has a distal wall 38 that is joined (typically welded) to the central support 30. The distal wall 38 has a distal projection 24. A mold releasing agent can be applied to the distal projection 24 so that after the molding process, the flexible tip 22 would be free to rotate about the distal projection 24. The central support 30 has a central lumen which surrounds the guide wire 60. At its proximal end, the central support 30 is welded to a wound metal torque cable 32 which extends outside the body (as shown in FIG. 11).

The distal portion of the shielding catheter 40 consists of a shield 50 to protect a limited arc of arterial wall from being atherectomized and a distal guiding ring 54 to guide the cutting cylinder 26 directly back when cutting. The shielding catheter 40 also includes a proximal ring 52 to enclose the cutting edge 27 of the cutting cylinder 26 when the SPAC 10 is in the closed position and a blade guide 56 to insure that the cutting cylinder 26 is guided properly into its closed position. The blade guide 56 also is used with fluoroscopy to insure proper cutting of plaque from an eccentric stenosis by indicating the angular location of the shield 50. The proximal ring 52 also acts to securely hold onto a plastic cylinder 40. Further the SPAC 10 is designed so that the distal end of the distal ring 54 will engage the shoulder 23 of the flexible tip 22 before the cutting edge 27 comes in contact with the annular surface 53 of the proximal ring 52. Thus the cutting edge 27 will not be made dull by contacting the surface 53.

It should be understood that instead of having a complete 360 degree distal guiding ring 54, the shield 50 could have an angular arc of just over 180 degrees at its distal end and that would accomplish the same purpose of guiding the cutting cylinder 26. Furthermore, if the blade guide 56 was considerably extended in the distal direction, one could properly guide the cutting cylinder 26 back to nest into the proximal ring 52 even if the cylindrical arc of shield 50 was considerably less than 180 degrees.

As can be seen in FIGS. 1, 4, 5 and 6, the proximal ring 52, the shield 50 and the distal guiding ring 54 would typically be formed from a thin-walled metal cylinder with a longitudinal cutout or window. The shield 50 is in the form of a cylindrical arc of metal that would remain after metal was removed from the thin-walled cylinder to form the longitudinal cutout cylinder as illustrated in FIGS. 1, 4, 5 and 6.

At its proximal end (which is shown in FIG. 11), the plastic cylinder 42 of the shielding catheter 40 extends outside of the patient's body. Located between the outer surface of the torque cable 32 and the inner surface of the plastic cylinder 42 is an annular lumen 44 used to inject liquids into the artery and to exert a negative pressure (vacuum) on the arterial segment to be atherectomized. Within the wall of the plastic cylinder 42 is a lumen 47 which extends through most of the length of the plastic cylinder 42 and is used to inflate and deflate the occlusive balloon 48 located near the distal end of the plastic cylinder 42. The hole 46 connects the lumen 47 to the interior chamber of balloon 48. The occlusive balloon 48 when inflated, will create a pressure seal against the inside wall of the artery. The dotted lines in FIG. 1 indicate the position of the balloon 48 when it is expanded.

Located between the outer surface of the central support 30 and the inner surface of the cutting cylinder 26 is the plaque collection chamber 28. When the atherectomy procedure is completed, the SPAC 10 will be in the closed position as shown in FIG. 1, and the plaque that is to be cut and collected will lie within the plaque collection chamber 28. Because the central support 30 prevents the cut plaque in the plaque collection chamber 28 from making contact with the guide wire 60, the guide wire 60 can remain in place while the SPAC 10 is removed from the artery. It should be noted that in FIG. 1 the exterior surface of the SPAC 10 is continuous, i.e. in its closed position the SPAC has no open window or cutout that would prevent easy Dottering through a tight stenosis.

Figure 2:
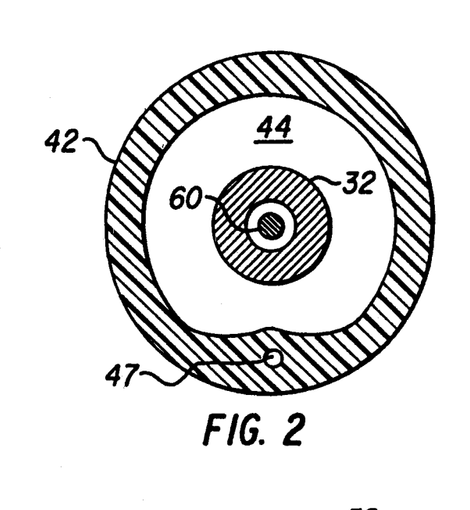
FIG. 2 is an enlarged transverse cross section of the SPAC proximal to the occluding balloon at 2—2 of FIG. 1.

FIG. 2 shows the transverse cross section of the SPAC proximal to the location of the occlusive balloon. At this location the plastic cylinder 42 contains a lumen 47 used to inflate and deflate the occlusive balloon 48 shown in FIG. 3. Inside the plastic cylinder 42 is the torque cable 32. Between the outside of the torque cable 32 and the inside of the plastic cylinder 42 is the annular lumen 44. Inside the torque cable 32 is the guide wire 60.

Figure 3:
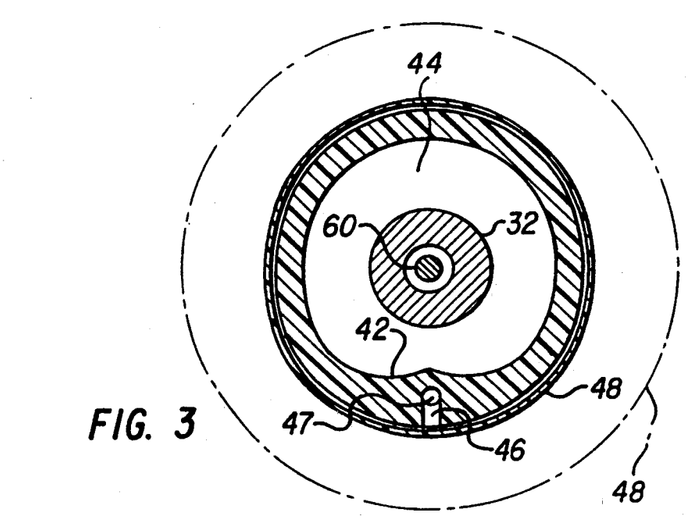
FIG. 3 is an enlarged transverse cross section of the SPAC at the center of the occluding balloon at 3—3 of FIG. 1.

FIG. 3 shows the transverse cross section of the SPAC 10 at the position of the occlusive balloon 48. FIG. 3 shows the plastic cylinder 42, the hole 46 and the lumen 47 within the wall of the plastic cylinder 42 used to inflate and deflate the occlusive balloon 48. The outline of the occlusive balloon 48 when inflated is shown as a dotted line in FIG. 3.

Figure 4:
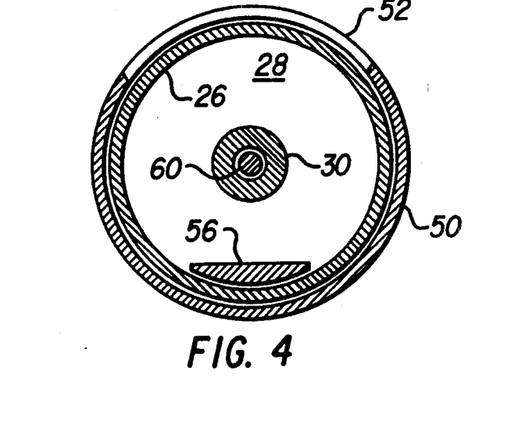
FIG. 4 is an enlarged transverse cross section of the distal end of the SPAC at 4—4 of FIG. 1 which illustrates the shield, blade guide, and cutting cylinder.
Figure 6:
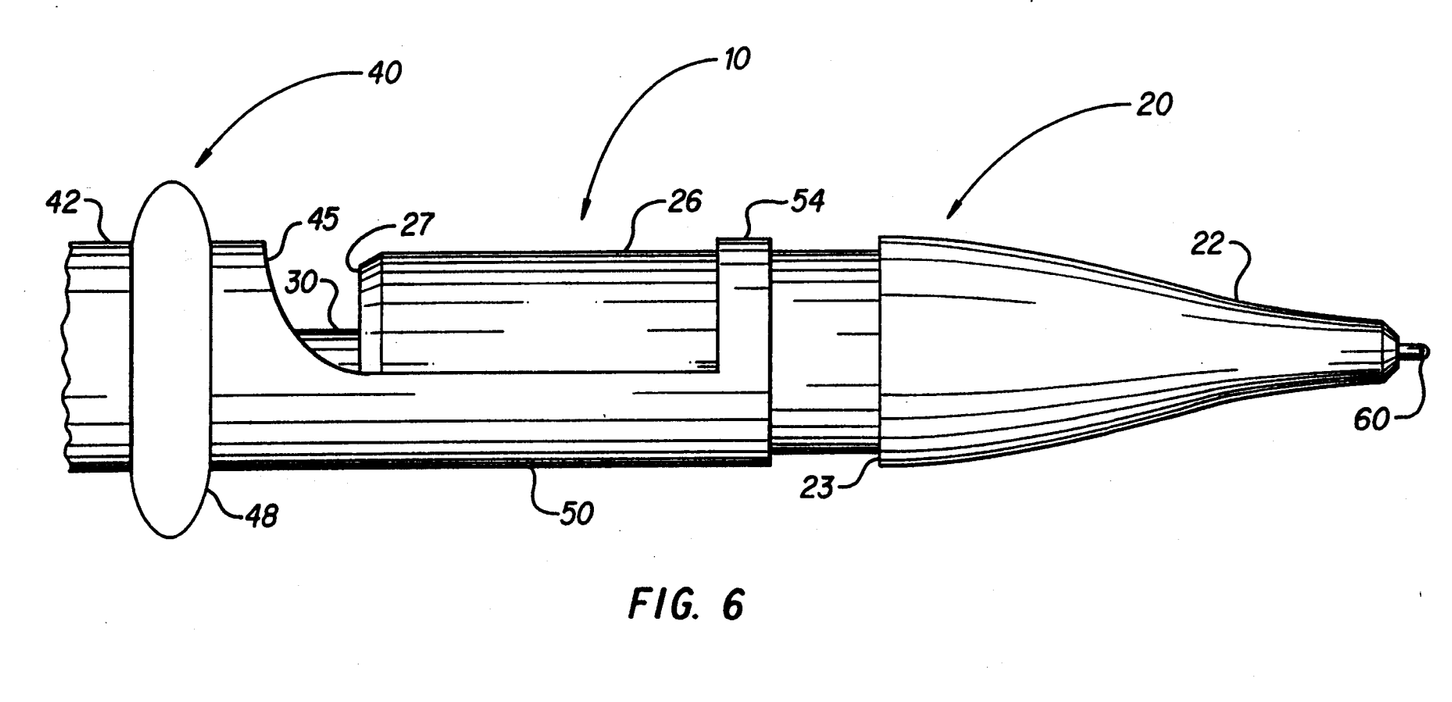
FIG. 6 is a side view of the SPAC shown partially open to show the shape of the shield.

FIG. 4 shows the transverse cross section of the SPAC (in its closed condition) distal to the end of the plastic cylinder 42. FIG. 4 shows the shield 50 near its proximal end where it has an arc length of approximately 270 degrees. This design allows the cutting cylinder 26 to be accurately guided to its closed position within the proximal ring 52. FIG. 6 provides a side view to better illustrate the shape of the shield 50. FIG. 4 also shows the transverse cross section of the blade guide 56, the plaque collection chamber 28, the central support 30 and guide wire 60, and further shows the distal edge of the proximal ring 52.

Figure 5:
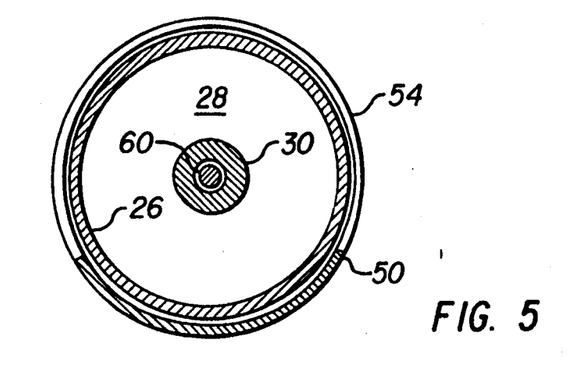
FIG. 5 is an enlarged transverse cross section of the distal end of the SPAC at 5—5 of FIG. 1 which illustrates the shield and cutting cylinder.

FIG. 5 shows the transverse cross section of the SPAC (in its closed position) at the center of the shield. At this point and over most of its length, the shield 50 shields an arc length of less than 180 degrees (typically 90 to 120 degrees) of the artery wall from being atherectomized by the cutting cylinder 26. In fact the shield 50 might have an arc length as small as 45 degrees or as large as 270 degrees depending on how one might wish to excise plaque from a stenosis. FIG. 5 also shows the guiding ring 54, the cutting cylinder 26, the plaque collection chamber 28, the central support 30 and the guide wire 60.

FIG. 6 is a side view of the SPAC 10 in a partially open position. FIG. 6 shows the cut/collect catheter 20 having a flexible tip 22 shaped for effective Dottering through a tight stenoses and for tracking well over the guide wire 60. Also shown is the cutting cylinder 26 with cutting edge 27 and central support 30. As the spinning cutting cylinder 26 is pulled back (cutting plaque as it goes) the guide ring 54 of the shield 50 keeps the cutting cylinder 26 centered inside the distal end of the shielding catheter 40. As the cutting edge 27 nears the proximal end of the shield 50, the tapered shape 45 of the shield 50 guides the cutting cylinder 26 into its closed position. The occlusive balloon 48 (shown inflated here) near the distal end of the plastic cylinder 42 can be used to make a pressure seal against the artery proximal to the stenosis being atherectomized.

Figure 7:
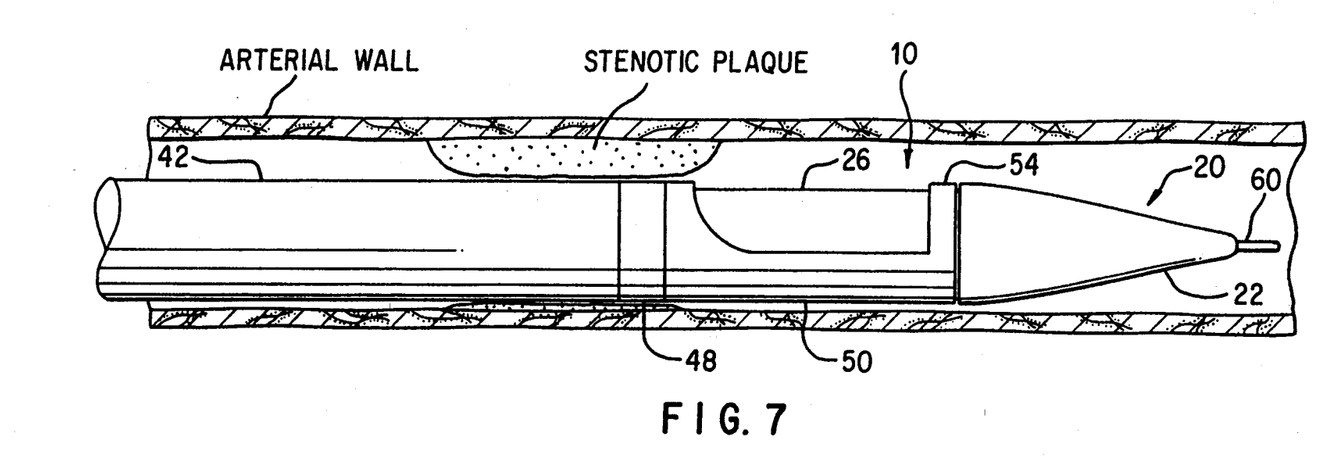
FIG. 7 is a side view of the SPAC shown in its closed position within a stenosis in an artery.

FIG. 7 illustrates the position of the SPAC 10 after it has Dottered through an eccentric stenosis showing significantly more plaque toward one side of the artery than the other. The SPAC 10 is pushed forward along the guide wire 60 until the proximal end of the shield 50 is just distal to the stenosis.

Figure 8:
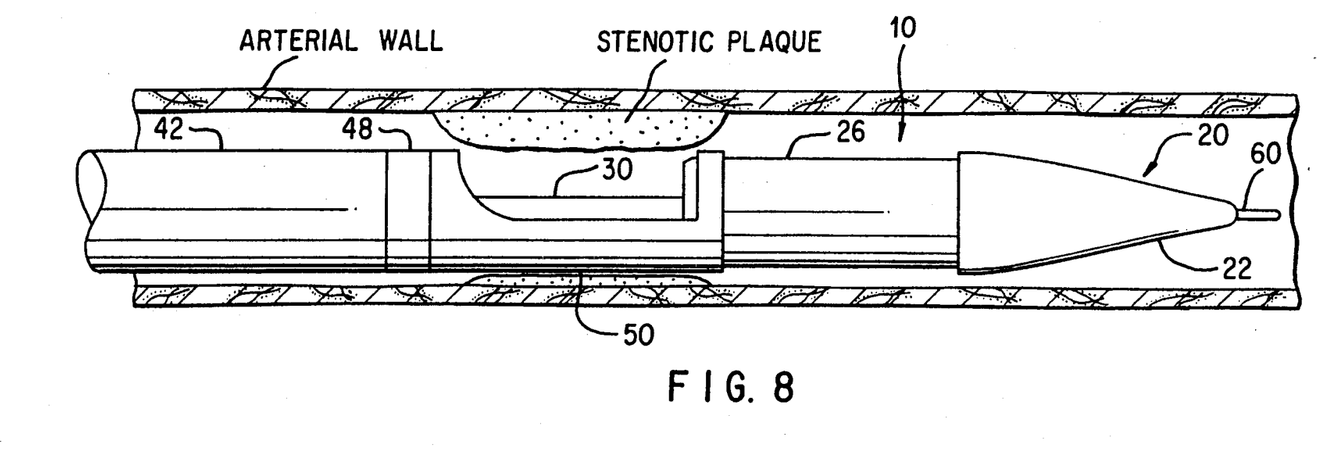
FIG. 8 is a side view of the SPAC in the open position within an artery.

FIG. 8 illustrates the SPAC system 10 after the shielding catheter's plastic cylinder 42 has been pulled back and rotated until the shield 50 is opposite the eccentric plaque to be removed.

Figure 9:
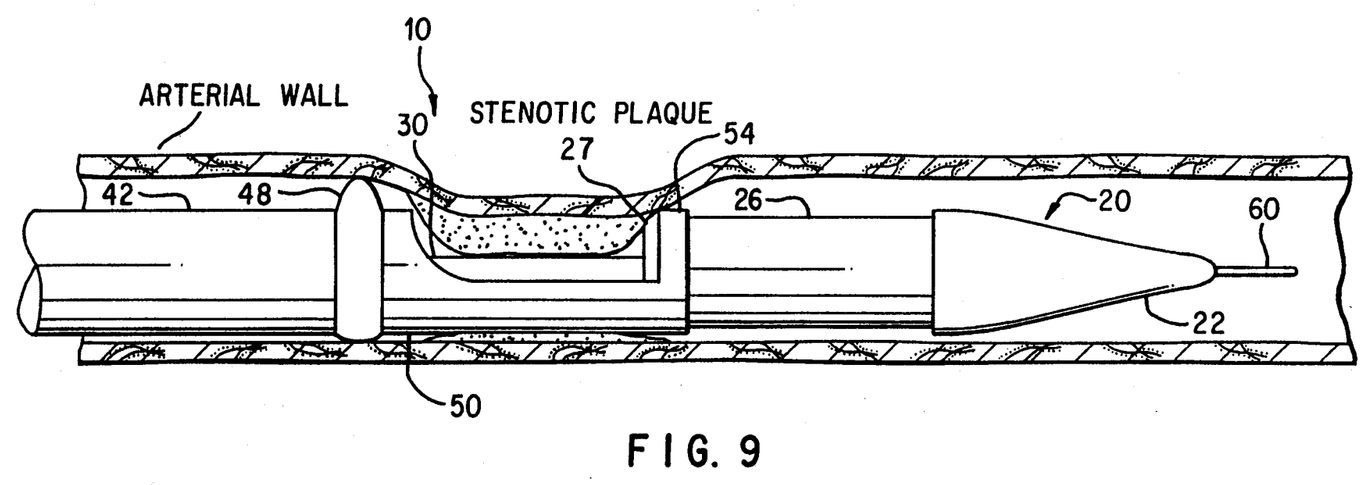
FIG. 9 is a side view of the SPAC with the occlusive balloon inflated and vacuum applied to the arterial segment.

FIG. 9 illustrates the effect on the artery of the SPAC 10 after the occlusive balloon 48 has been inflated and vacuum has been applied to the arterial segment which includes the stenotic plaque. When vacuum is applied, the artery will constrict, forcing the plaque in against the central cylinder 30.

Figure 10:
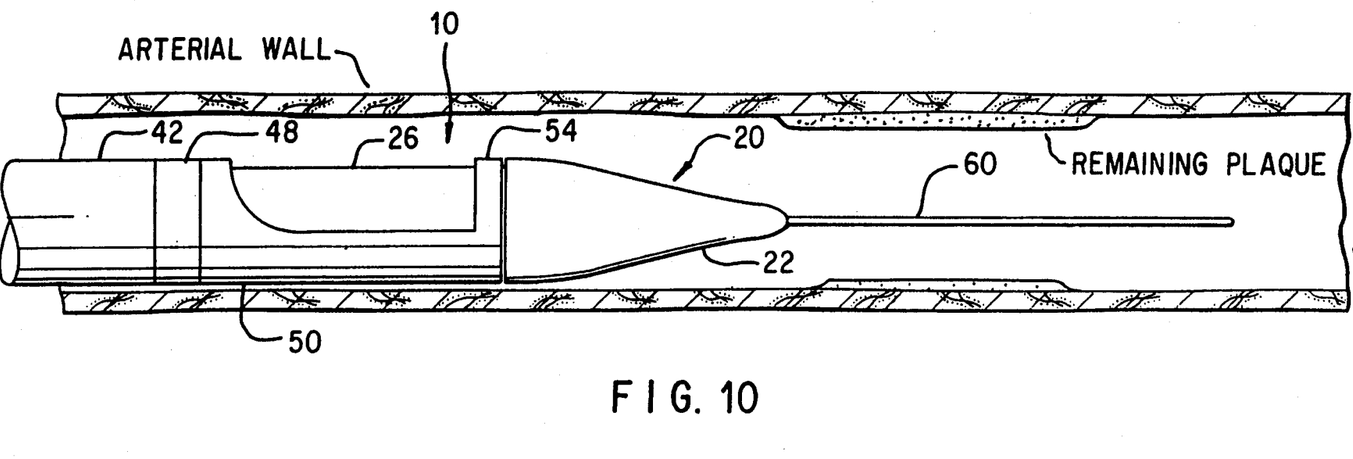
FIG. 10 is a side view of the SPAC showing the catheter pulled back and closed and the vacuum turned off.

FIG. 10 illustrates the SPAC system 10 after the cutting cylinder 26 is pulled back while rotating to cutout the precise thickness of plaque that is situated between the cylindrical outer surface of the central support 30 and the cutting edge 27. The shield 50, shields the side of the eccentric stenosis with the minimum amount of plaque (or none) from being atherectomized. FIG. 10 shows the SPAC 10 in its closed position proximal to the atherectomized stenosis. In this condition, the cut plaque is within the plaque collection chamber 28 awaiting removal from the body.

All metal parts of the SPAC 10 would typically be made from type 304 stainless steel except for the cutting cylinder 26 and the shield 50 which would typically be made from type 455 stainless steel that has been heat treated for maximum hardness. All plastic parts of the SPAC 10 would be polyurethane, polyethylene, PVC or a similar type of medically acceptable plastic.

FIG. 11 shows the SPAC 10 being used for atherectomy in a human leg. Outside the body at the proximal end of the SPAC 10 there are two tubes attached namely: the tube 62 which is in fluid communication with the annular lumen 44 and is used to inject saline, contrast, and other liquids and also used to provide vacuum to the cutting site; and the occlusive balloon inflation tube 64 which is in fluid communication with the lumen 47 and is used to provide pressure and suction to inflate and deflate the occlusive balloon 48 near the distal end of the plastic cylinder 42. The box 66 in FIG. 11 represents a source of fluid or vacuum, and the box 68 represents a source of fluid for inflating the occlusive balloon 48 or a suction source for deflating the balloon 48. The torque cable 32 extends beyond the attached tubes and is connected to a rotator 70 used to spin the cut/collect catheter 20 to enhance cutting the plaque. Extending beyond the proximal end of the rotator 70 is the guide wire 60.

Although the discussion herein is principally concerned with a catheter that cuts in the retrograde direction, the invention that is taught herein is equally applicable to atherectomy catheters that cut in the anterograde direction such as that described in the Fischell et al U.S. Pat. No. 4,898,575 or the Simpson European Patent Application No. 0,163,502. Furthermore, various blade configurations such as those described in the prior art (e.g. multiple separate blades or serrated blades) could be used in conjunction with the technique for shielding the blade and constricting the artery using vacuum as described herein. Furthermore, ablation techniques such as using grinding, laser vaporization or high energy ultrasonic vibrators could be used successfully with the shielding and vacuum techniques described herein.

Figures 12, 13:
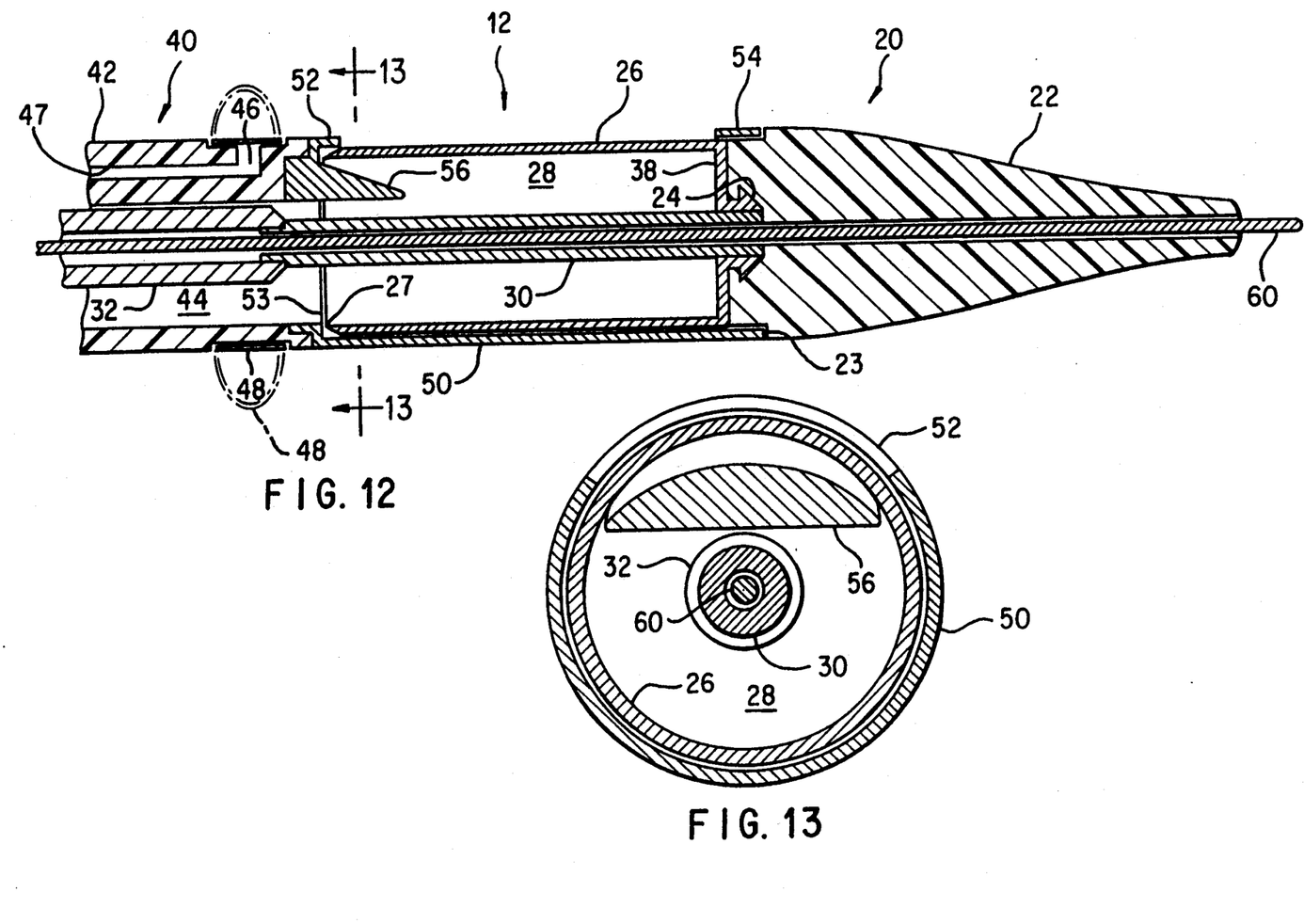
FIG. 12 shows the longitudinal cross section of another embodiment of the SPAC with the blade guide oriented opposite the shield for better cutter rescue capability.
FIG. 13 is an enlarged transverse cross section of one SPAC embodiment at 13—13 of FIG. 12 to illustrate the tapered shape of the blade guide.

FIG. 12 shows the longitudinal cross section of another embodiment of the SPAC 12 opposite the shield 50. The advantage of this embodiment is that the blade guide 56 not only guides the cutting cylinder 26 into the closed position, but it can be used to rescue the cutting cylinder 26 if it is blocked by some hard calcified plaque by moving distally against that hard calcified plaque. Rescue is then accomplished by pushing the shielding catheter 40 (with its tapered distal end) distally until the SPAC 12 is closed. Then the continuous outer surface of the SPAC 12 allows easy withdrawal from the artery.

FIG. 13 is a transverse cross section of the SPAC 12 embodiment of FIG. 12 which illustrates the tapered shape of the blade guide 56.

Figure 14:
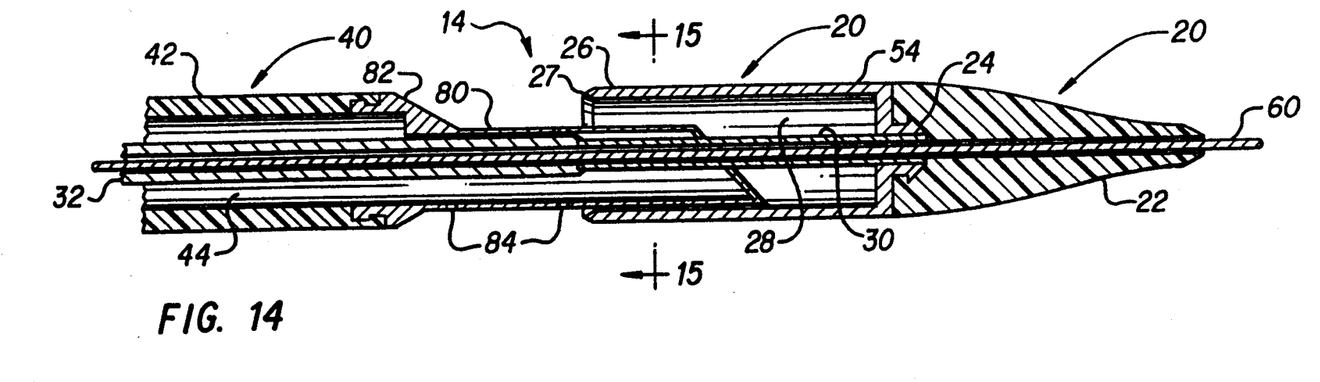
FIG. 14 shows the longitudinal cross section of another embodiment of the SPAC in a partially open position (as if it were cutting) where the shield is located inside the cutting cylinder instead of outside the cutting cylinder as in previous embodiments.

FIG. 14 shows the longitudinal cross section of another embodiment of the SPAC 14 in a partially open position (as if it were cutting) where the shield 80 is located inside the cutting cylinder 26 instead of outside the cutting cylinder 26 as in previous embodiments. Through holes 84 in the shield 80 are used to provide access to the annular lumen 44 of the shielding catheter 40 for infusing liquids into the artery and for applying vacuum. The proximal end 82 of the shield 80 provides a tapered means to connect the shield 80 to the plastic cylinder 42. Although no occlusive balloon is shown in FIG. 14, it can of course be added.

Figure 15:
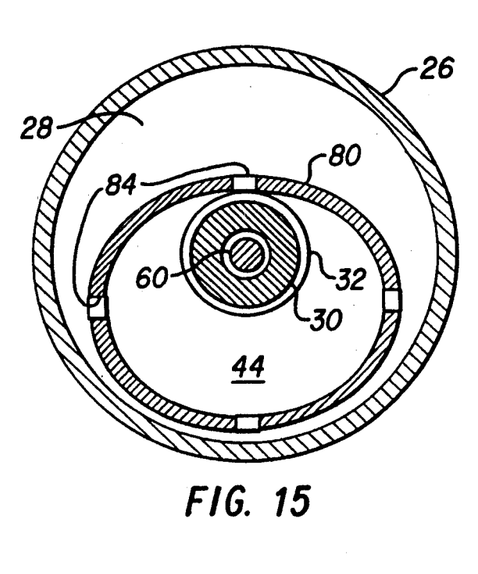
FIG. 15 shows an enlarged transverse cross section of the SPAC at 15—15 in FIG. 14 and illustrates a possible shape for the shield.

FIG. 15 is a transverse cross section of the SPAC 14 at 15—15 in FIG. 14 where the shield 80 is located inside the cutting cylinder 26. FIG. 15 illustrates one possible shape for the shield 80, although other shapes are clearly possible.

Figure 16:
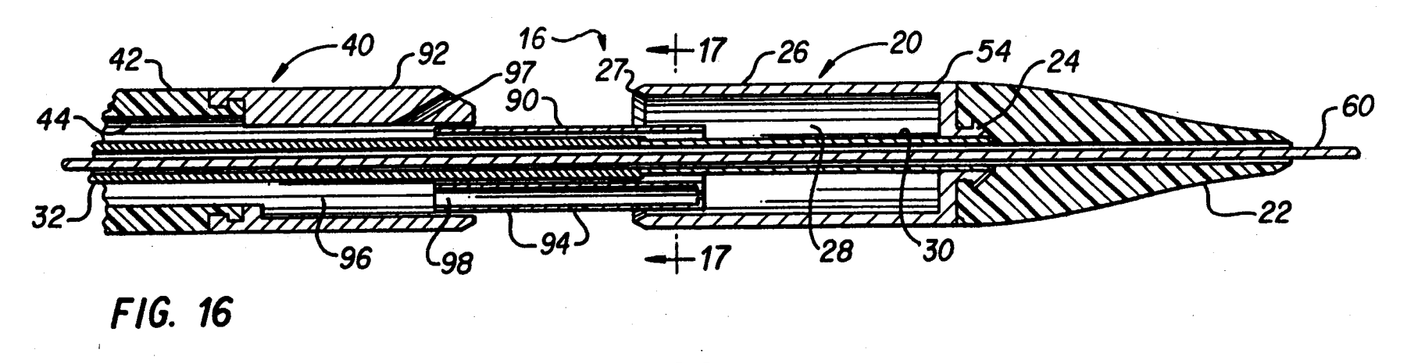
FIG. 16 shows the longitudinal cross section of still another embodiment of the SPAC system in a partially open position (as if it were cutting) in which the inside shield slides along a shield guide which runs along the longitudinal axis of the distal end of the shielding catheter.

FIG. 16 shows the longitudinal cross section of still another embodiment of the SPAC system 16 in a partially open position (as if it were cutting) in which the inside shield 90 slides along a shield guide 96 which runs along the longitudinal axis of the distal end of the shielding catheter 40. A fluid passageway 98 in the shield 90 allows liquid to flow into and out out of the through holes 94 for infusing liquids into the artery and applying vacuum. An additional fluid passageway 97 in the distal ring 92 of the shielding catheter 40 also is used for infusing liquids into the artery and applying vacuum. The shield 90 fits like a key in the shield guide 96 located in the distal ring 92 of the shielding catheter 40. Although no occlusive balloon is shown in FIG. 16, it can of course be added.

Figure 17:
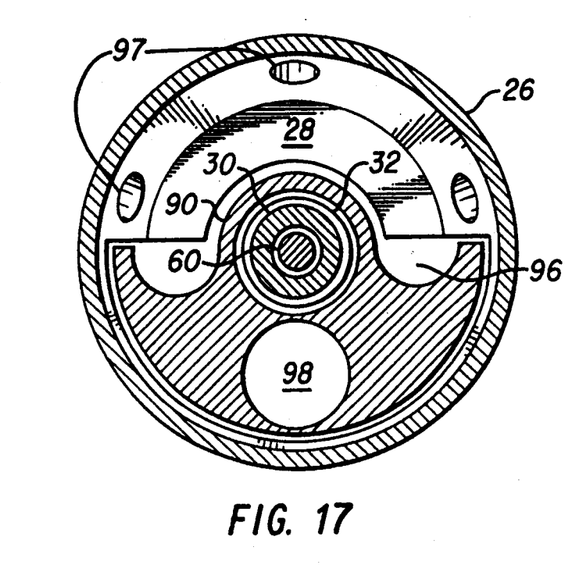
FIG. 17 shows an enlarged transverse cross section of the SPAC at 17—17 of FIG. 16 illustrating a possible shape for the shield and the shield guide.

FIG. 17 is a transverse cross section of the SPAC system at 17—17 in FIG. 16 illustrating a possible shape for the shield 90 and the shield guide 96.

The discussion herein has been focused on the use of a longitudinal cylindrical arc of metal called a shield to prevent a portion of an arterial wall from being exposed to the cutting edge of the SPAC. Based on the teachings herein one could readily use a SPAC having a 120 degree arc of shield to remove all plaque from a concentric stenosis by using two successive atherectomy procedures. The first procedure would be as described herein, The SPAC would then be rotated 180 degrees and a second atherectomy procedure would be performed to remove plaque on the opposite side of the stenosis. Thus definitive atherectomy of concentric stenoses could be preformed with only two such procedures. This would be an advantage over a shield that is, for example a 240 degree arc which would require four or more procedures to completely remove plaque from the periphery of an artery.

Further, it should be understood that the pullback atherectomy catheter as described in U.S. patent application Ser. No. 447,187, now U.S. Pat. No. 5,011,490 by Robert E. Fischell and Tim A. Fischell entitled "Endoluminal Tissue Excision Catheter and Method", which is included herein by reference, could be used with a vacuum source as described herein to accomplish the technique of Vacuum Pullback Atherectomy (VPA).

Still further it should be understood that the SPAC as taught herein could be used with the compressional techniques described in the previously mentioned U.S. patent application Ser. No. 577,633 to accomplish compressional atherectomy of eccentric (or concentric) stenoses.

Although all the description herein has been relevant to the excision of stenotic plaque from human arteries, it should be understood that the catheters described herein could be used to safely remove obstructive tissue from many types of vessels in living bodies including those in animals as well as in human beings. For example, the catheter described herein could be used to excise tissue from the urethra, fallopian tubes or other vessels of a human being or an animal.

Various other modifications, adaptations and alternative designs are, of course possible in light of the above teachings. Therefore it should be understood at this time that within the scope of the appended claims, the invention may be practiced otherwise than as specifically described herein.

What is claimed is:

1. A catheter for excision of obstructive tissue from a vessel of a living body comprising:

a flexible guide wire adapted to be advanced through the obstructive tissue in the vessel of the living body so that the guide wire's distal end is positioned beyond the obstructive tissue;

a cut/collect catheter having a hollow torque cable surrounding said flexible guide wire and displaceable with respect thereto, said hollow torque cable having a proximal end adapted to lie outside of the living body and a distal end fixedly coupled to a central support of a cutting cylinder at a distal end thereof for rotative displacement of said cutting cylinder, said cutting cylinder having at least one tapered sharpened cutting edge at the cutting cylinder's proximal end, the cutting edge being capable of cutting obstructive tissue off the vessel wall as it is pulled back in a retrograde direction, the cutting cylinder having attached at its distal end a hollow, tapered, flexible, elastomer tip which is adapted to penetrate through and beyond the obstructive tissue, the interior surface of the cutting cylinder forming a tissue collection chamber which is completely closed except at its proximal end and into which collection chamber all of the cut off obstructive tissue is collected, the cut/collect catheter further having a continuous central passageway which is adapted to be advanced over the guide wire, the continuous central passageway extending from the proximal end of the hollow torque cable to the distal end of the hollow elastomer tip so as to prevent contact between the outer surface of the guide wire and the cut off obstructive tissue; and a shielding catheter adapted to move slideably over and to fit concentrically around the cut/collect catheter for most of the length of the cut/collect catheter that is adapted to lie inside the vessel, the shielding catheter consisting for most of its length of a plastic cylinder which has a metal cutout cylinder having a proximal ring portion, said metal cutout cylinder being fixedly attached to the plastic cylinder's distal end, the metal cutout cylinder having a longitudinal cutout wherein the metal is removed except for a partial-cylindrical arc portion which forms a shield to prevent cutting of an arc of the vessel wall, said longitudinal cutout being shorter in length as compared to the length of the cutting cylinder at its outermost diameter, said flexible tip having a shoulder formed therein for engagement of the distal edge of the metal cutout cylinder thereto.

2. The catheter of claim 1 wherein the metal cutout cylinder has a distal guiding ring at the cutout cylinder's distal end, the guiding ring being adapted to surround and move slideably over the cut/collect catheter's cutting cylinder.

3. The catheter of claim 1 further comprising a rotating means situated outside of the living body and attached to the proximal end of the torque cable, the rotating means being adapted to rotate the cutting cylinder as the cutting edge is pulled back in a retrograde direction through the obstructive tissue.

4. The catheter of claim 1 further comprising a blade guide located at the proximal end of the shielding catheter's metal cutout cylinder, the blade guide being adapted to force the cutting edge of the cutting cylinder to nest within said proximal ring portion of the metal cutout cylinder.

5. The catheter of claim 1 wherein an annular lumen is formed between the outer surface of the cut/collect catheter's torque cable and the inner surface of the shielding catheter's plastic cylinder so that fluid communication is obtained from the shielding catheter's proximal end through to the shielding catheter's distal end.

6. The catheter of claim 5 further comprising a source of fluid operably connected to the shielding catheter's proximal end for injecting fluid through the annular lumen and out of the shielding catheter's distal end portion.

7. The catheter of claim 5 including a source of suction operably connected to the shielding catheter's proximal end for establishing a vacuum at the distal end of the shielding catheter.

8. A catheter for excision of obstructive tissue from a vessel of a living body comprising:

a flexible guide wire adapted to be advanced through the obstructive tissue in the vessel of the living body so that the guide wire's distal end is positioned beyond the obstructive tissue;

a cut/collect catheter having a hollow torque cable surrounding said flexible guide wire and displaceable with respect thereto, said hollow torque cable having a proximal end adapted to lie outside of the living body and a distal end fixedly coupled to a central support of a cutting cylinder at a distal end thereof for rotative displacement of said cutting cylinder, said cutting cylinder having at least one tapered sharpened cutting edge at the cutting cylinder's proximal end, the cutting edge being capable of cutting obstructive tissue off the vessel wall as it is pulled back in a retrograde direction, the cutting cylinder having attached at its distal end a hollow, tapered, flexible elastomer tip having a shoulder section, said flexible tip adapted to penetrate through and beyond the obstructive tissue, the interior surface of the cutting cylinder forming a tissue collection chamber which is completely closed except at its proximal end and into which collection chamber all of the cut off obstructive tissue is collected the cut/collect catheter further having a continuous central passageway which is adapted to be advanced over the guide wire, the continuous central passageway extending from the proximal end of the hollow torque cable to the distal end of the hollow elastomer tip so as to prevent contact between the outer surface of the guide wire and the cut off obstructive tissue; and a shielding catheter adapted to move slideably over and to fit concentrically around the cut/collect catheter for most of the length of the cut/collect catheter that is adapted to lie inside the vessel, the shielding catheter consisting for most of its length of a plastic cylinder which has a metal cutout cylinder having a proximal ring portion, said metal cutout cylinder being fixedly attached to the plastic cylinder's distal end, said flexible tip shoulder section being engaged to the distal edge of the cutout cylinder for preventing said cutting cylinder cutting edge from contacting said cutout cylinder proximal ring portion, the metal cutout cylinder having a longitudinal cutout wherein the metal is removed except for a partial-cylindrical arc portion which forms a shield to prevent cutting of an arc of the vessel wall, said cutting cylinder having an outer surface which fits snugly inside the cutout cylinder of the shielding catheter so as to form an essentially continuous exterior surface of the catheter so as to minimize the force required to push the cutout through the obstructive tissue and further minimize the torque required when the catheter's distal end where the cutout is placed is rotated within the obstructive tissue.

9. The catheter of claim 8 wherein the cutting cylinder of the cut/collect catheter has a central passageway formed from a metal cannula which cannula prevents the cut obstructive tissue that is cut and collected within the cutting cylinder from making contact with the outer surface of the guide wire.

10. The catheter of claim 8 wherein the included angle of the partial-cylindrical arc of the shield is less than 180 degrees.

11. The catheter of claim 8 wherein the included angle of the partial-cylindrical arc of the shield is less than 120 degrees.

12. The catheter of claim 8 wherein the shielding catheter includes an inflatable balloon located just proximal to the proximal end of the cutout.

13. A catheter for excision of obstructive tissue from a vessel of a living body comprising:

a flexible guide wire adapted to be advanced through the obstructive tissue in the vessel of the living body so that the guide wire's distal end is positioned beyond the obstructive tissue;

a cut/collect catheter having a hollow torque cable whose proximal end is adapted to lie outside of the living body and whose distal end is fixedly connected to the distal end of a cutting cylinder which has at least one sharpened cutting edge at the cutting cylinder's proximal end, the cutting edge being capable of cutting obstructive tissue off the vessel wall as it is pulled back in a retrograde direction, the cutting cylinder having attached at its distal end a hollow, tapered, flexible, elastomer tip which is adapted to penetrate through and beyond the obstructive tissue, the interior surface of the cutting cylinder forming a tissue collection chamber which is completely closed except at its proximal end and into which collection chamber all of the cut off obstructive tissue is collected, the cut/collect catheter further having a continuous central passageway which is adapted to be advanced over the guide wire, the continuous central passageway extending from the proximal end of the hollow torque cable to the distal end of the hollow elastomer tip so as to prevent contact between the outer surface of the guide wire and the cut off obstructive tissue; and a shielding catheter adapted to move slideably over and to fit concentrically around the cut/collect catheter for most of the length of the cut/collect catheter that is adapted to lie inside the vessel, the shielding catheter consisting for most of its length of a plastic cylinder which has a metal cutout cylinder having a proximal ring portion, said metal cutout cylinder being fixedly attached to the plastic cylinder's distal end, the metal cutout cylinder having a longitudinal cutout wherein the metal is removed except for a partial-cylindrical arc portion which forms a shield to prevent cutting of an arc of the vessel wall, said longitudinal cutout being shorter in length as compared to the length of the cutting cylinder at its outermost diameter, said tip having a radially extending shoulder adapted to engage the distal edge of the shielding catheter's metal cutout cylinder in order to prevent the cutting cylinder's cutting edge from contacting the metal cutout cylinder's proximal ring portion thereby preventing dulling of the cutting edge.

* * * * *